(12) United States Patent
Dusterhoft et al.

(10) Patent No.: US 12,357,349 B2
(45) Date of Patent: Jul. 15, 2025

(54) EN BLOC CONNECTOR

(71) Applicant: Astura Medical Inc., Iriving, TX (US)

(72) Inventors: Ross Dusterhoft, Irving, TX (US); Thomas Purcell, Irving, TX (US)

(73) Assignee: ASTURA MEDICAL INC., Irving, TX (US)

( * ) Notice: Subject to any disclaimer, the term of this patent is extended or adjusted under 35 U.S.C. 154(b) by 384 days.

(21) Appl. No.: 17/989,643

(22) Filed: Nov. 17, 2022

(65) Prior Publication Data
US 2023/0149054 A1    May 18, 2023

Related U.S. Application Data

(60) Provisional application No. 63/281,067, filed on Nov. 18, 2021.

(51) Int. Cl.
*A61B 17/70* (2006.01)
*A61B 17/00* (2006.01)
*A61B 90/00* (2016.01)

(52) U.S. Cl.
CPC ........... *A61B 17/7077* (2013.01); *A61B 2017/00991* (2013.01); *A61B 2090/0811* (2016.02)

(58) Field of Classification Search
CPC ............... A61B 17/7077; A61B 17/02
See application file for complete search history.

(56) References Cited

U.S. PATENT DOCUMENTS

| | | | |
|---|---|---|---|
| 4,220,146 A * | 9/1980 | Cloutier | A61B 17/6425 606/90 |
| 2001/0016741 A1 | 8/2001 | Burkus | |
| 2006/0247645 A1 | 11/2006 | Wilcox | |
| 2008/0119862 A1 | 5/2008 | Wicker | |
| 2014/0257312 A1 | 9/2014 | Solitario, Jr. | |
| 2019/0110785 A1 | 4/2019 | Serokosz et al. | |

OTHER PUBLICATIONS

International Search Report and Written Opinion in PCT Application No. PCT/US22/50324 dated Sep. 13, 2023.

* cited by examiner

*Primary Examiner* — Andrew Yang
(74) *Attorney, Agent, or Firm* — Michael R Shevlin

(57) ABSTRACT

An En Bloc connector configured to couple with multiple sequential reducers or extenders, such as spinal screw reducers, to correct a rotation deformity of the spine by turning or rotating the deformed spine structure toward a normal position. In the embodiments shown, the En Bloc connector holds three sequential reducers in the retracted configuration and four sequential reducers in the extended configuration.

17 Claims, 6 Drawing Sheets

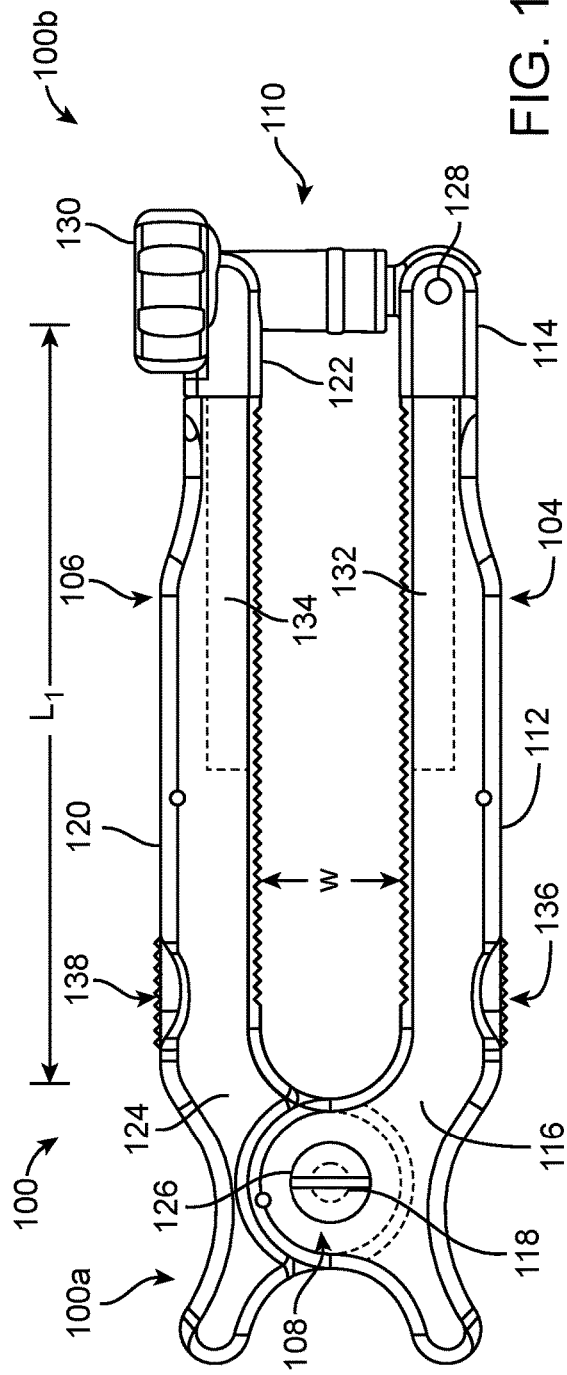
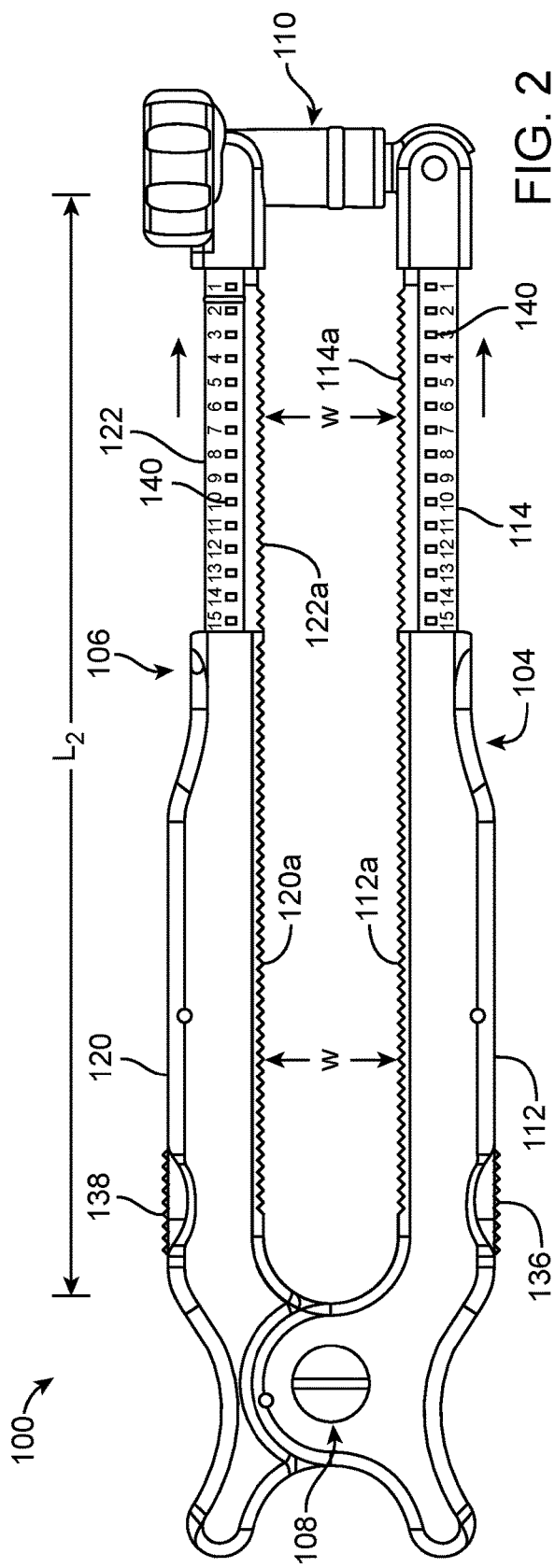

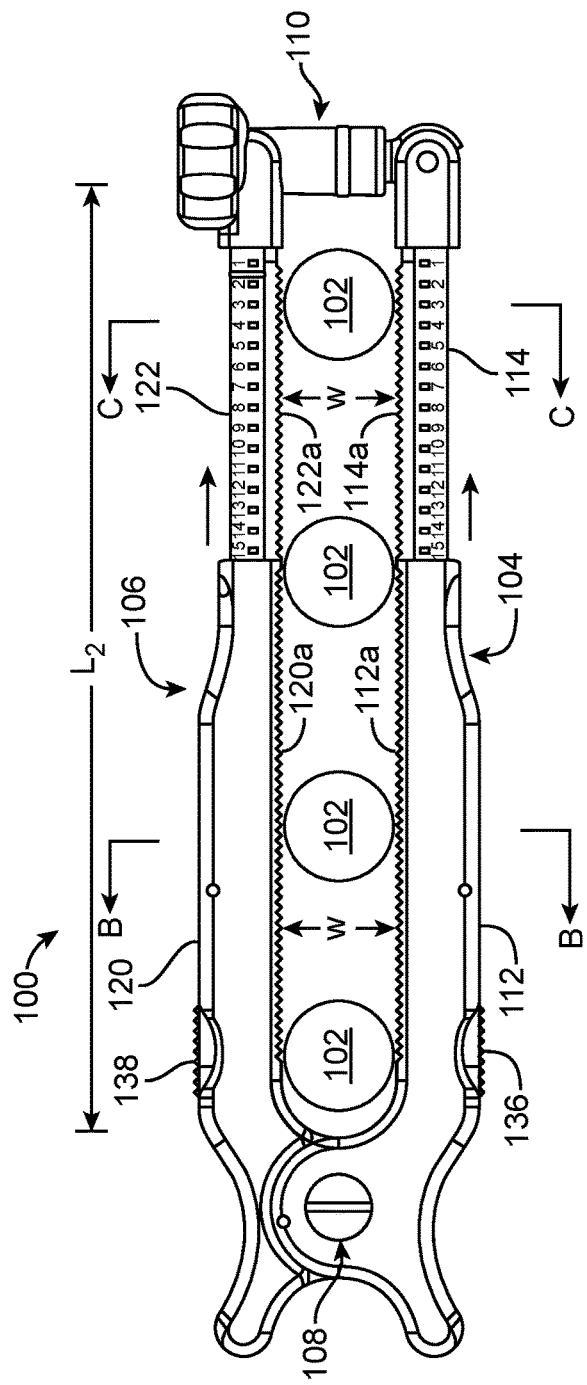
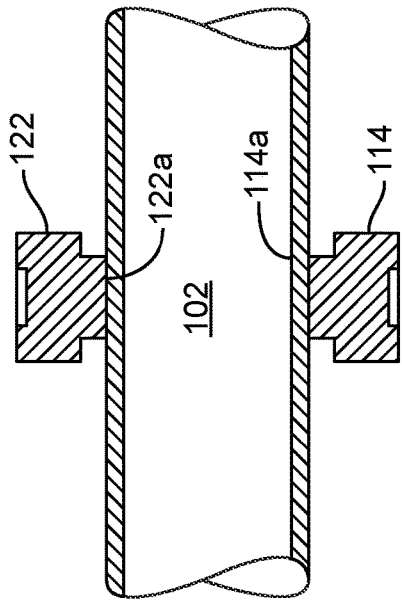
FIG. 5
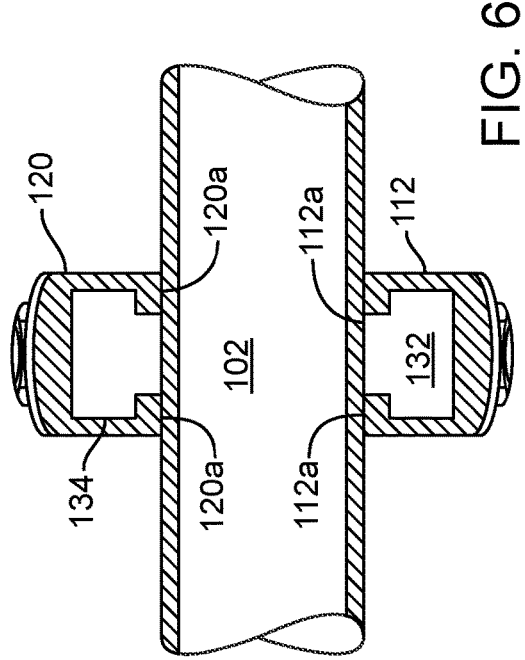
FIG. 6
FIG. 7

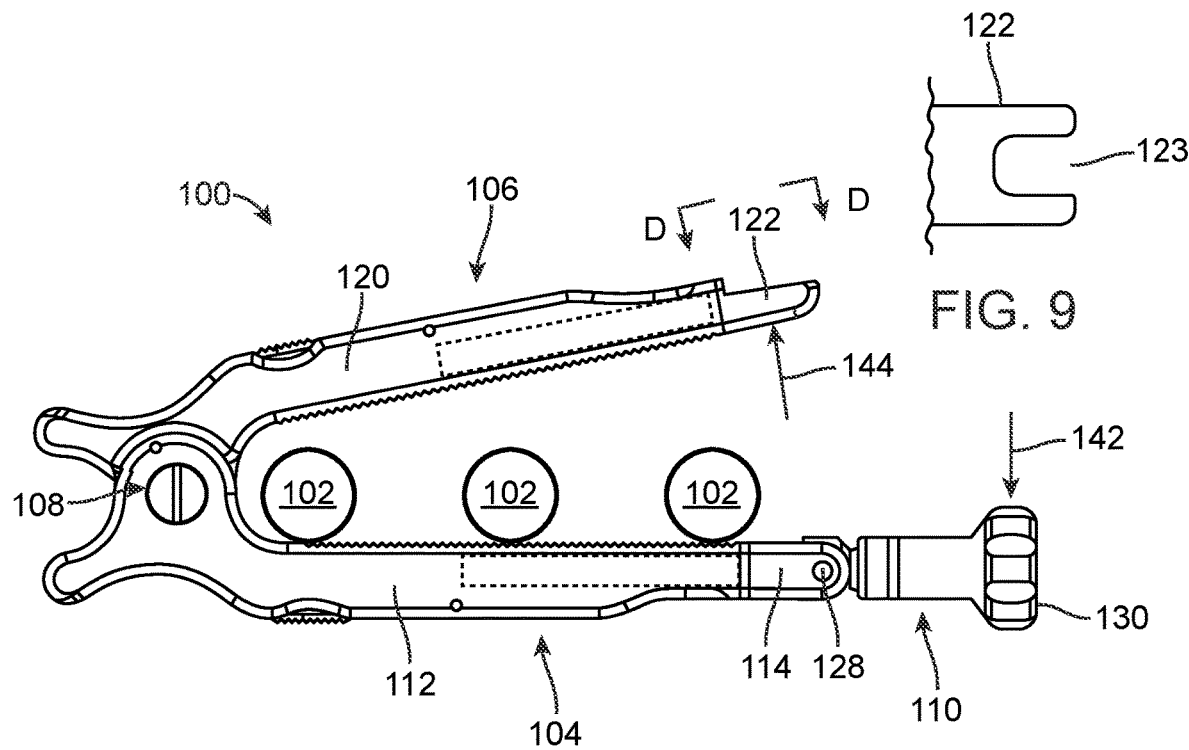
FIG. 9
FIG. 8
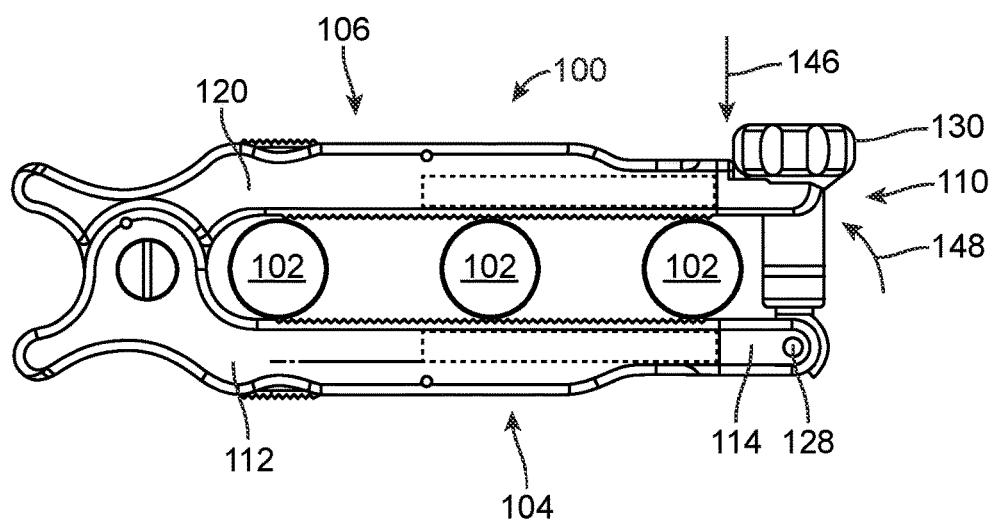
FIG. 10

EN BLOC CONNECTOR

CROSS-REFERENCE TO RELATED APPLICATIONS

This application claims the benefit of U.S. Provisional Application No. 63/281,067 filed Nov. 18, 2021, which is incorporated herein by reference.

FIELD

The present invention relates generally to the field of surgery, and more specifically, to En Bloc connector for use with reducers in spinal fusion surgery.

BACKGROUND

The spine is a series of individual bones called vertebrae. A normal spine has no side-to-side curve but does have a series of front-to-back curves, giving it a gentle "S" shape. Many people have an abnormal curvature of the spine and it may be necessary to straighten or adjust the spine into a proper curvature and alignment.

Spinal surgical procedures have been developed to correct the abnormal curvature of the spine. One procedure involves placing multiple pedicle screws into the vertebrae of the curved region and coupling spinal fixation rods to the screw heads. The rods are shaped to mimic the normal curvature and force the spine into proper alignment once positioned within the screw head. The rods are then secured or locked to the screws maintain the curvature.

The Spinal surgical procedures can require complex movement and manipulation of the vertebrae to restore normal curvature to the patient. The manipulation may include a rotational force applied on pedicle screws in the coronal plane (medial-laterally) is referred to as "derotation". This is usually done by applying compression and/or distraction forces of a derotation instrument to vertebrae via the screw extenders.

Current competitive deformity instrumentation, specifically in the sector of direct vertebrae rotation (DVR), lack the functional performance needed to meet current market needs. Current En Bloc offerings include connectors of varying sizes of fixed length that require the surgeon to have many sizes of connectors available. This results in the surgeon often having to test fit a size before finding the correct size. This is very inconvenient and time consuming during an operation.

Accordingly, there remains a need for instruments and methods that provide solutions to the problems of current systems. The present invention is directed toward meeting these needs.

SUMMARY

An En Bloc connector configured to couple with multiple sequential reducers or extenders, such as spinal screw reducers, to correct a rotation deformity of the spine by turning or rotating the deformed spine structure toward a normal position. In the embodiments shown, the En Bloc connector holds three sequential reducers in the retracted configuration and four sequential reducers in the extended configuration. In other embodiments, the En Bloc connector may a different number of sequential reducers, such as between 2 and twelve sequential reducers 102.

BRIEF DESCRIPTION OF THE DRAWINGS

FIG. 1 shows one embodiment of an En Bloc connector in a retracted configuration.

FIG. 2 shows the En Bloc connector in an extended configuration.

FIG. 5 shows one example of the En Bloc connector that has been extended to hold additional sequential reducers.

FIG. 6 is a sectional view at B-B of FIG. 5.

FIG. 7 is a sectional view at C-C of FIG. 5.

FIGS. 8-10 show some of the steps in loading sequential rod reducers in the En Bloc connector of FIG. 1.

DETAILED DESCRIPTION

Figure 3:
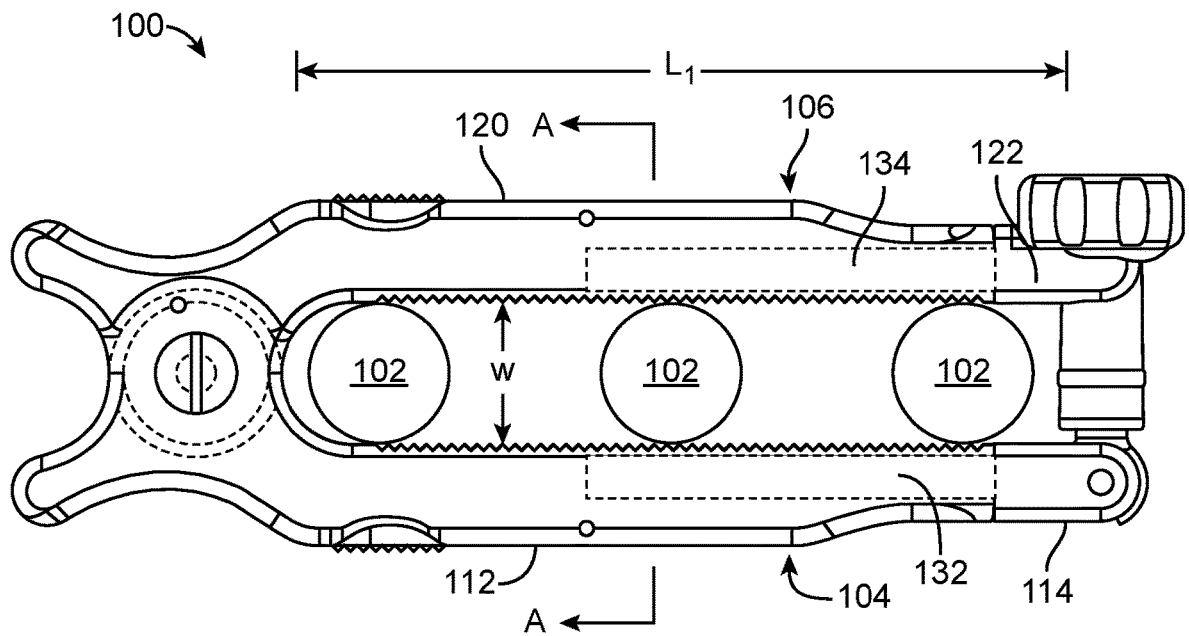
FIG. 3 shows one example of the En Bloc connector holding three sequential reducers.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

FIG. 1 shows one embodiment of an En Bloc connector 100 in a retracted configuration and FIG. 2 shows the En Bloc connector 100 in an extended configuration. The En Bloc connector 100 is configured to couple with multiple sequential reducers 102 or extenders, such as spinal screw reducers, to correct a rotation deformity of the spine by turning or rotating the deformed spine structure toward a normal position. In the embodiments shown, the En Bloc connector 100 holds three sequential reducers 102 in the retracted configuration and four sequential reducers 102 in the extended configuration. In other embodiments, the En Bloc connector 100 may a different number of sequential reducers 102, such as between 2 and twelve sequential reducers 102.

The En Bloc connector 100 includes a first arm 104 and a second arm 106 coupled to a first hinge pin 108 at a first end 100a and an arm closure mechanism 110 at a second end 100b. The arm closure mechanism may be an arm locking mechanism 110. The first and second arms 104, 106 of the En Bloc connector 100 are parallel and separated by a distance W and having a length L1, creating an area for multiple sequential reducers 102 to be locked in place.

The first arm 104 includes a first fixed portion 112 on a proximal end slidingly coupled to a first telescoping portion or first extendable portion 114 on a distal end. The second arm 106 includes a second fixed portion 120 on a proximal end slidingly coupled to a second telescoping portion or extendable portion 122 on a distal end. The proximal end of the first fixed portion 112 includes an inwardly curved portion 116 having a first pivot hole 118. The proximal end of the second fixed portion 120 includes an inwardly curved portion 124 having a second pivot hole 126. The inwardly curved portions 116, 124 of the first and second fixed portions 112, 124 are configured to overlap, and the first and second pivot holes 118, 126 are in alignment. The first hinge pin 108 is configured to fit the first and second pivot holes 118, 126 so that the first fixed portion 112 is rotatingly coupled to the second fixed portion 120 with the first hinge pin 108.

The first and second extendable portions 114, 122 are positioned within t-slots 132, 134 of the first and second fixed portions 112, 120. In the embodiment shown, the t-slots 132 can be other shapes of slots or recesses. The first and second fixed portions 112, 114 and first and second extendable portions 114, 122 include inwardly facing surfaces 112a, 114a. 120a, 122a designed to make contact with the sequential reducer 102. The design of the t-slots 134, 136 allow for the inward facing surfaces 112a, 114a, 120a, 122a to contact the sequential rod reducer 102 when the first and second fixed portions 112, 120 and first and second extendable portions 114, 122 are at any of its positions.

The En Bloc connector 100 include features to extend the length of the first and second arms 104, 106 from L1 (FIG. 1) to L2 (FIG. 2) to hold more sequential reducers 102. The first and second extendable portions 114, 122 are designed to slide from the first and second fixed portions 112, 120. The first and second extendable portions 114, 122 are locked within slots 132, 134 of the first and second fixed portions 112, 120 by first and second extendable portion locks or clips 136, 138. When the first and second extendable portion locks 136, 138 are depressed or squeezed inward toward each other, they disengage the first and second extendable portions 114, 122, allowing them to extend. When the desired extension length L2 is reached, the first and second extendable portion locks 136, 138 are released, and the extendable portions 114, 122 are locked in place. The extendable portions 114, 122 may be locked in incremental positions. The extendable portions 114, 122 may include laser markings 140 showing different positions or length marks.

The length L of the first and second extendable portions 104, 106 may be extended during surgery to hold more sequential reducers 102 without having to change to a different En Bloc connector 100.

The arm locking mechanism 110 is rotatingly coupled to the distal end of the first extendable portion 114 with a second hinge pin 128 and releasably coupled to the distal end of the second extendable portion 114 with an arm locking device 130, such as a knob. In some embodiments, the arm locking mechanism 110 may be tightened through a screw mechanism built within the arm locking mechanism 110. In some embodiments, the arm locking mechanism 110 snap fits into the second arm (106) to reach the "closed" or "locked" position.

When the arm locking device 130 is unlocked, the first and second arms 104, 106 are configured to rotate from the closed position to an open position, discussed below.

FIG. 3 shows one example of the En Bloc connector 100 holding three sequential reducers 102 or extenders between the first and second arms 104, 106. The inwardly facing surfaces 112a, 114a of the first and second fixed portions 112, 114 and the inwardly facing surfaces 120a, 122a of the first and second extendable portions 114, 122 contacting the sequential reducer 102. The design of the t-slots 132, 134 allow the inward facing surfaces of the first and second fixed portions 112, 120 and first and second extendable portions 114, 122 to contact the sequential reducers 102 at any of their positions between retracted and extended.

Figure 4:
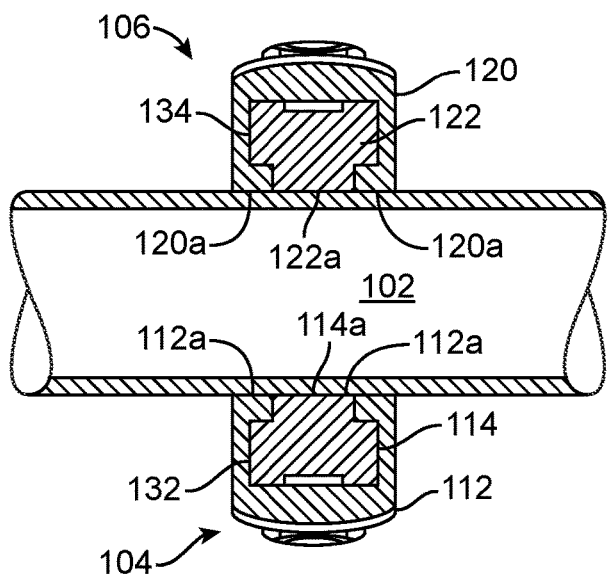
FIG. 4 is a sectional view at A-A of FIG. 3.

FIG. 4 is a sectional view at A-A showing features of the first and second arms 104, 106. In the embodiment shown, the first fixed portion 120 includes a t-slot 132 sized for the first extendable portion 114. The first fixed portion 112 and first extendable portion 114 include inwardly facing surfaces 112a, 114a designed to make contact with the sequential reducer 102. The second fixed portion 120 and second extendable portion 122 include inwardly facing surfaces 120a, 122a designed to make contact with the sequential reducer 102. The t-slots 132, 134 allow contact between the inwardly facing surfaces 112a, 114a, 120a, 123a and the sequential rod reducer 102 when the first and second fixed portions 112, 120 and first and second extendable portions 114, 122 are at any of their positions.

FIG. 5 shows one example of the En Bloc connector 100 that has been extended to hold additional sequential reducers 102, such as four sequential reducers 102, between the first and second arms 104, 106, with the first and second extendable portions 114, 122 in an extended position. The first and second extendable portions 114, 122 are locked within the first and second t-slots 132, 134 of the first and second fixed portions 112, 120 by the first and second extendable portion locks 136, 138. When the first and second extendable portion locks 136, 138 are depressed inward, they disengage from the first and second extendable portions 114, 122, allowing them to extend from the first and second fixed portions 112, 120. In some embodiments when the locking mechanism is locked, the lengths of the first and second extendable portions 114, 122 may be adjusted at the same time. When the desired extension is reached, the first and second extendable portion locks 136, 138 are released and lock the extendable portions 114, 122 with the first and second fixed portions 112, 120. The extendable portions 114, 122 may be locked in incremental positions. The extendable portions 114, 122 may include laser markings 140 showing different positions or distances. The laser marks may also show additional information.

FIG. 6 is a sectional view at B-B showing the first and second fixed portions 112, 120 holding the sequential reducers 102. The extendable portions have been extended, leaving the t-slots 132, 134 empty. The inwardly facing surfaces 112a, 120a making contact with the sequential reducers 102.

FIG. 7 is a sectional view at C-C showing the first and second extendable portions 114, 122 in the extended position with the inwardly facing surfaces 114a, 122a making contact with the sequential reducer 102.

As discussed above, t-slots allow for contact between the first and second fixed portion surfaces 112a, 120a and first and second extendable portion surfaces 114a, 122a to make contact with the sequential rod reducer 102 when the first and second fixed portions 112, 120 and first and second extendable portions 114, 122 are at any of its positions.

FIGS. 8-10 show some of the steps in loading sequential rod reducers 102 in the En Bloc connector 100 of FIG. 1.

FIG. 8 shows the arm locking mechanism 110 unlocked from the second extendable portion 122 and rotated downward 142. The second arm 106 is rotated upward 144, so that the En Bloc connector 100 is in the open position. FIG. 9 shows the end of the second extendable portion 122 having a slot or opening 123 sized to engage the arm locking mechanism 110. FIG. 10 shows the En Bloc connector 100 with three sequential rod reducers 102.

Once the arm locking mechanism 110 unlocked it is rotated downward 142 and the second arm 106 may be rotated upward 144, positioning the En Bloc connector 100 in the open position. The second end 100b of the En Bloc connector is now open for insertion of the sequential rod reducers 102. FIG. 10 shows the sequential rod reducers 102 in place and the second arm 106 is rotated downward 146 until the inwardly facing surfaces 120a, 122a engage the sequential rod reducers 102. The arm locking mechanism 110 is then rotated upward 148 and the arm locking device 130 engages slot 123 locks to the second extendable portion 122. The En Bloc connector 100 is now ready for use.

Figure 11:
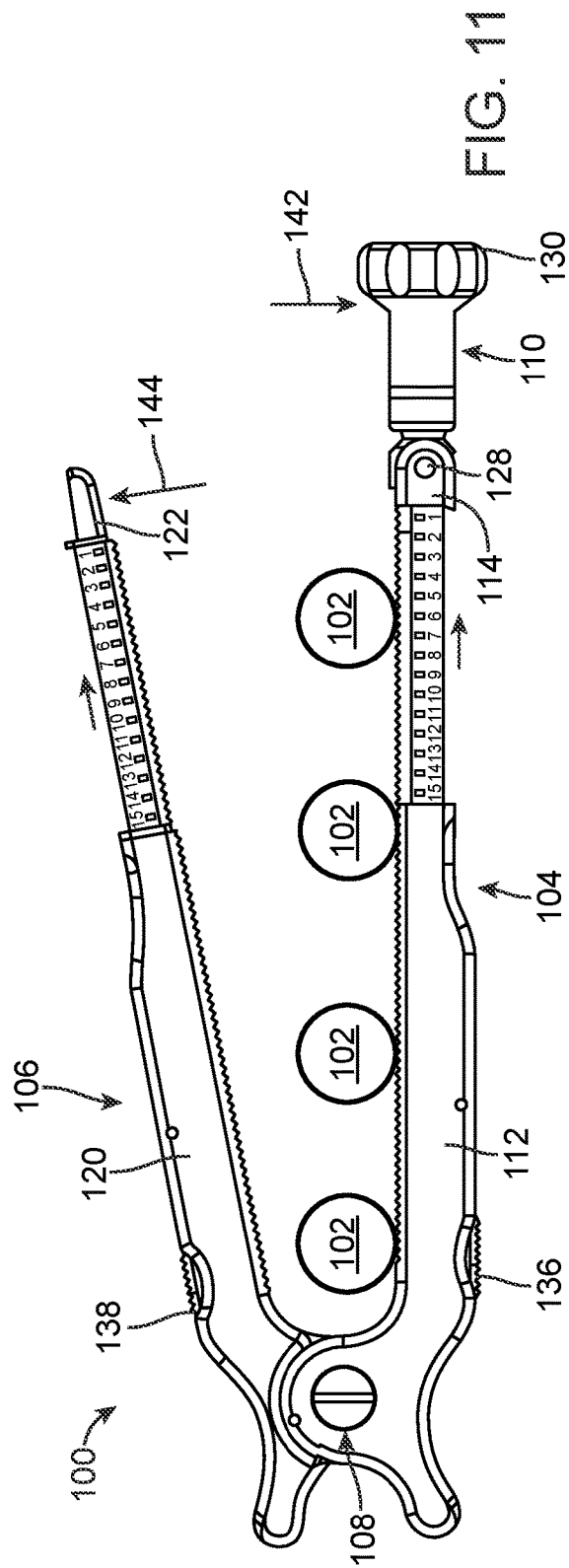
FIGS. 11 and 12 show some of the steps in loading sequential rod reducers in the extended En Bloc connector of FIG. 3.
Figure 12:
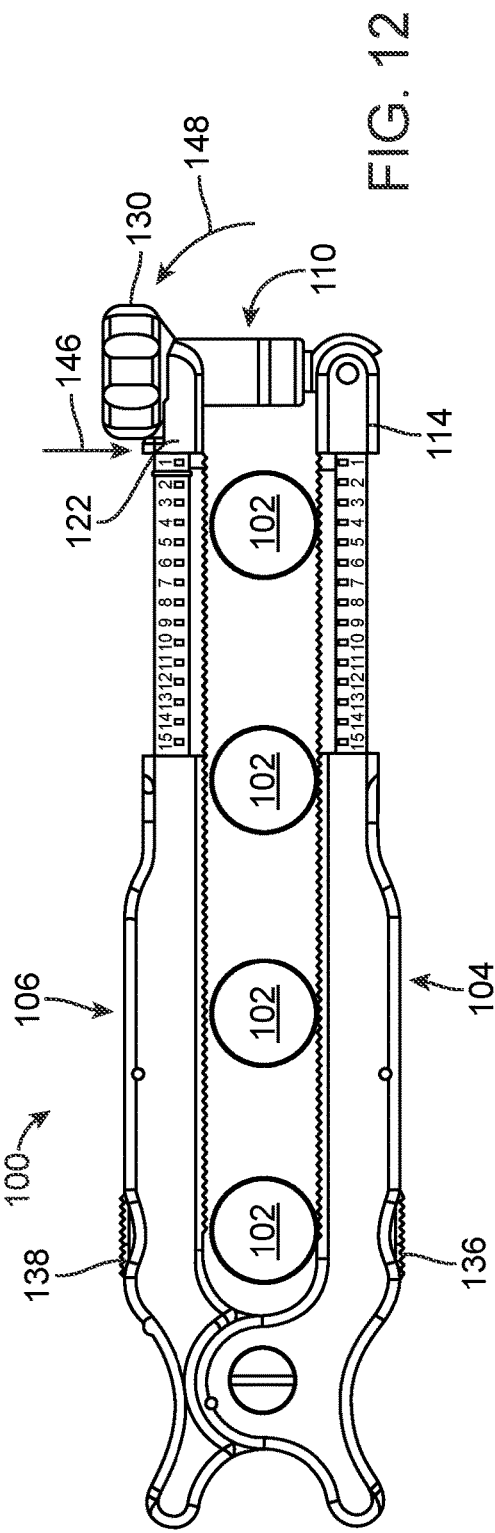

FIGS. 11 and 12 show some of the steps in loading sequential rod reducers 102 in the extended En Bloc connector 100 of FIG. 3.

In FIG. 11 shows the arm locking device 130 unlocked from the second extendable portion 122 and rotated downward 142 and the second arm 106 is rotated upward 144, positioning the En Bloc connector 100 in the open position. The second end 100b of the extended En Bloc connector 100 is open for insertion of the sequential rod reducers 102. FIG. 12 shows the sequential rod reducers 102 in place and the second arm 106 is rotated downward 146 until the inwardly facing surfaces 120a, 122a engage the sequential rod reducers 102. The arm locking mechanism 110 is then rotated upward 148 and the arm locking device 130 engages slot 123 locks to the second extendable portion 122. The extended En Bloc connector 100 is now ready for use.

Figure 13:
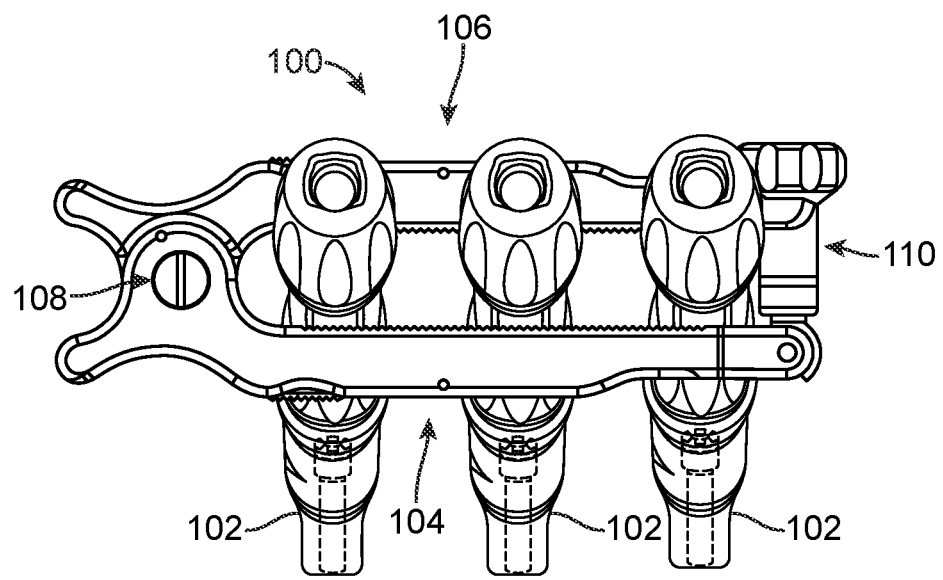
FIGS. 13 and 14 show two different configurations of the En Bloc connector.
Figure 14:
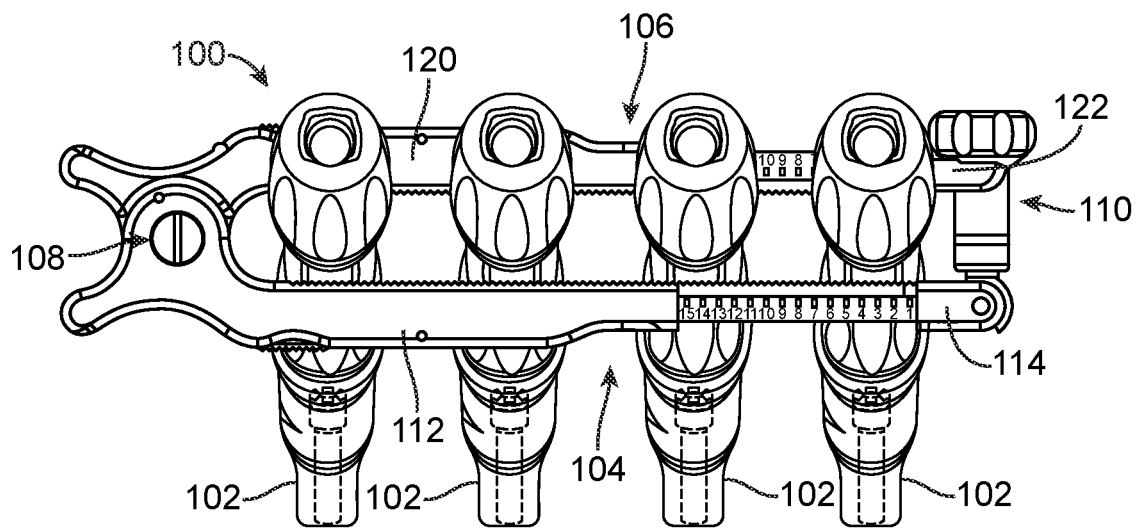

FIGS. 13 and 14 show two different configurations of the En Bloc connector 100. FIG. 13 shows a first a first configuration of the En Bloc connector 100 with the first and second arms 104, 106 not extended and holding three sequential rod reducers 102. FIG. 14 shows a second configuration of the En Bloc connector 100 with the first and second arms 104, 106 extended and holding four sequential rod reducers 102.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An En Bloc connector for spinal fusion surgery comprising:
    a first extendable arm having a proximal end and a distal end, the first extendable arm being configured to extend from a retracted position L1 to an extended position L2;
    a second extendable arm having a proximal end and a distal end, the first extendable arm being configured to extend from a retracted position L1 to an extended position L2;
    the proximal end of the first extendable arm is configured to couple with the proximal end of the second extendable arm, and the distal end of the first extendable arm being configured to couple with distal end of the second extendable arm,
    wherein the proximal ends of the first and second extendable arms are rotatably coupled, and the distal ends of the first and second extendable arms are coupled with an arm locking mechanism and
    an area is formed between the coupled first and second extendable arms for multiple reducers;
    the first and second extendable arms include inwardly facing surfaces designed to make contact with the multiple reducers between the retracted position L1 and the extended position L2.

2. The En Bloc connector of claim 1, wherein the first extendable arm includes a first fixed portion on the proximal end slidingly coupled to a first extendable portion on the distal end, and the second extendable arm includes a second fixed portion on the proximal end slidingly coupled to a second extendable portion on the distal end.

3. The En Bloc connector of claim 2, wherein the first and second extendable portions are positioned within t-slots of the first and second fixed portions.

4. The En Bloc connector of claim 3, wherein the design of the t-slot allows for the inward facing surfaces to make contact with the multiple reducers when the first and second fixed portions and first and second extendable portions are at any extended position.

5. The En Bloc connector of claim 3, wherein the first and second extendable portions are locked within t-slots of the first and second fixed portions by first and second extendable portion locks.

6. The En Bloc connector of claim 5, wherein the first and second extendable portion locks are configured to be unlock to allow the first and second extendable portions extend and relock the first and second extendable portions when a desired extension length is reached.

7. The En Bloc connector of claim 6, wherein the first and second extendable portion locks are configured to lock the first and second extendable portions in incremental positions.

8. The En Bloc connector of claim 7, wherein the first and second extendable portions have markings showing the incremental positions.

9. The En Bloc connector of claim 1, wherein when the arm locking mechanism is unlocked, the first and second extendable arms are configured to rotate from a closed position to an open position.

10. An En Bloc connector for spinal fusion surgery comprising:
a first arm having a first fixed portion on a proximal end slidingly coupled to a first extendable portion on a distal end, the first extendable portion being configured to extend from a retracted position L1 to an extended position L2;
a second arm having a second fixed portion on a proximal end slidingly coupled to a second extendable portion on a distal end, the second extendable portion being configured to extend from a retracted position L1 to an extended position L2;
the first and second arms are configured to be coupled at the proximal and distal ends forming an area is formed between the coupled first and second arms for multiple reducers;
wherein the proximal ends of the first and second extendable arms are rotatably coupled, and the distal ends of the first and second extendable arms are coupled with an arm locking mechanism; and
the first and second fixed portions and first and second extendable portions include inwardly facing surfaces designed to make contact with the multiple reducers between the retracted position L1 and the extended position L2.

11. The En Bloc connector of claim 10, wherein the first and second extendable portions are positioned within t-slots of the first and second fixed portions.

12. The En Bloc connector of claim 11, wherein the design of the t-slot allows for the inward facing surfaces to make contact with the multiple reducers when the first and second fixed portions and first and second extendable portions are at any extended position.

13. The En Bloc connector of claim 11, wherein the first and second extendable portions are locked within t-slots of the first and second fixed portions by first and second extendable portion locks.

14. The En Bloc connector of claim 13, wherein the first and second extendable portion locks are configured to be unlock to allow the first and second extendable portions extend and relock the first and second extendable portions when a desired extension length is reached.

15. The En Bloc connector of claim 14, wherein the first and second extendable portion locks are configured to lock the first and second extendable portions in incremental positions.

16. The En Bloc connector of claim 15, wherein the first and second extendable portions have markings showing the incremental positions.

17. The En Bloc connector of claim 10, wherein when the arm locking mechanism is unlocked, the first and second extendable arms are configured to rotate from a closed position to an open position.

* * * * *